United States Patent [19]

Tarnowski et al.

[11] Patent Number: 5,370,993
[45] Date of Patent: Dec. 6, 1994

[54] REVERSIBLE AGGLUTINATION MEDIATORS

[75] Inventors: Thomas L. Tarnowski, South San Francisco; Cheng-I Lin, San Jose; Edwin F. Ullman, Atherton, all of Calif.

[73] Assignee: Syntex (U.S.A.) Inc., Palo Alto, Calif.

[21] Appl. No.: 881,987

[22] Filed: May 12, 1992

Related U.S. Application Data

[62] Division of Ser. No. 278,870, Dec. 1, 1988, Pat. No. 5,136,095, which is a division of Ser. No. 51,978, May 19, 1987, Pat. No. 4,812,401.

[51] Int. Cl.$^5$ ............................................. G01N 33/53
[52] U.S. Cl. ........................................ 435/7.21; 435/4;
435/7.25; 436/519; 436/520; 436/526; 436/531;
436/534; 436/808; 436/829; 210/222; 210/223;
210/695; 210/704; 210/705; 210/710; 209/5;
209/214
[58] Field of Search ................. 435/7.21, 4, 7.25, 7.92,
435/7.93, 7.94, 975; 436/520, 519, 526, 531,
529, 534, 829, 808, 536, 538, 539; 210/222, 223,
695, 704, 705, 710; 209/5, 214

[56] References Cited

U.S. PATENT DOCUMENTS

| | | | |
|---|---|---|---|
| 2,648,710 | 8/1953 | Morrison et al. | 564/295 |
| 2,807,910 | 8/1957 | Erickson | 47/58 |
| 3,931,319 | 1/1976 | Green et al. | 564/286 |
| 3,970,518 | 7/1976 | Giaever | 435/239 |
| 4,115,534 | 9/1978 | Ithakissios | 424/1 |
| 4,230,685 | 8/1980 | Senyei et al. | 424/12 |
| 4,271,053 | 6/1981 | Kelsey et al. | 524/610 |
| 4,369,226 | 1/1983 | Rembaum | 428/334 |
| 4,452,773 | 6/1984 | Molday | 424/1.37 |
| 4,454,234 | 6/1984 | Czerlinski | 436/526 |
| 4,523,996 | 6/1985 | Charles et al. | 210/504 |
| 4,526,681 | 7/1985 | Friedlaender et al. | 209/214 |
| 4,687,748 | 8/1987 | Schroder | 436/526 |
| 4,780,421 | 10/1988 | Kameda et al. | 436/518 |
| 4,935,147 | 6/1990 | Ullman et al. | 210/695 |

FOREIGN PATENT DOCUMENTS

| | | |
|---|---|---|
| 0230768A1 | 8/1987 | European Pat. Off. . |
| 43197 | 7/1960 | Poland . |
| 2019378A | 10/1979 | United Kingdom . |
| 2152664A | 8/1985 | United Kingdom . |

*Primary Examiner*—Esther M. Kepplinger
*Assistant Examiner*—Susan C. Wolski
*Attorney, Agent, or Firm*—Shelley G. Precivale; Mark L. Bosse; Carole F. Barrett

[57] ABSTRACT

Compounds and methods are disclosed for reversibly aggregating particles suspended in a liquid medium. The method comprises combining the liquid medium containing the particles with a polyionic polymer capable of aggregating the particles under conditions suitable for such aggregation. Thereafter, the particles are contacted with a chemical reagent capable of cleaving the polyionic polymer under conditions sufficient to reverse the aggregation. Optionally, magnetic particles are added to the liquid medium in the present method under conditions for non-specific binding and the medium including the aggregates is subjected to a magnetic field gradient to separate the aggregates from the medium. The compounds of the present invention are polyions. The aggregation of the particles is reversible upon contact with chemical agents which cleave at least some of the bonds within the polyionic polymer.

17 Claims, No Drawings

REVERSIBLE AGGLUTINATION MEDIATORS

This is a divisional of Ser. No. 278,870, filed Dec. 1, 1988, now U.S. Pat. No. 5,136,095, which issued on Aug. 4, 1992, which in turn is a divisional of Ser. No. 07/051,978, filed May 19, 1987, now U.S. Pat. No. 4,812,401, which issued on Mar. 14, 1989, the disclosures of which are incorporated herein by reference.

BACKGROUND OF THE INVENTION

1. Field of the Invention

This invention relates to methods for reversibly aggregating particles that are dispersed in a liquid medium by use of a polyionic polymer to aggregate the particles and a chemical reagent to reverse the aggregation of the particles by cleaving at least some of the bonds within the polyionic polymer. The invention has particular application to separation of cells from biological fluids such as whole blood, lymphatic fluid, urine, cell cultures, etc.

Numerous techniques are known for determining the presence and amount of an analyte in a sample, such as a biological fluid, for example, blood or urine. An in vitro assay procedure is the most common of these techniques. Many of these techniques involve competitive binding of the analyte to be determined and a labeled analog of such analyte to binding sites on a specific receptor, for example, an antibody. Some of these techniques involve an aggregation step where the bound or unbound labeled analog is bound to or associated with a support such as a particle, which becomes aggregated. The aggregate can then be examined for a signal produced in relation to the amount of analyte in the sample.

Several techniques are known for aggregating particles suspended in a liquid medium. For example, the particles may be aggregated by employing a polymer in the medium. In other instances, the particles may be co-aggregated with magnetic particles using a polymer which, for example, non-specifically binds the particles and the magnetic particles.

Several techniques are known for separating bound and unbound fractions. For example, such techniques include differential migration of the bound and the free fractions, e.g., chromatoelectrophereses, gel filtration, etc., chemical precipitation of the bound or free fraction, e.g., by means of organic solvents, salts, acids, etc. followed by filtration or centrifugation; immunological precipitation of the bound fraction, e.g. by double antibody technique followed by filtration or centrifugation; absorption of the bound or free fraction onto selective sorbing media, e.g., charcoal, silicates, resins, etc.; magnetic separation techniques, and the like.

Magnetic separations generally fall into two general categories. There are those separations in which the material to be separated is intrinsically magnetic. The second type involves rendering one or more components of a mixture magnetic by attachment to a magnetically responsive entity. In biological separations, for example, materials of interest are generally not sufficiently magnetic and therefore, magnetic particles bound to antibodies, lectins and other targeting molecules have been used to isolate many of these materials.

The binding of non-magnetic and magnetic particles to each other can be affected by pH. Therefore, one method that has been suggested for reversing the aggregation of the particles involves altering pH. Binding can also be affected by other factors such as ionic strength and the presence of ionic or non-ionic polymers. In one approach, where the particles are bound by ionic interactions, the ionic strength is adjusted upwards to facilitate reversal of the coupling of the non-magnetic particles and the magnetic particles.

2. Description of the Related Art

A method for determining the concentration of substances in Biological fluids (e.g., drugs, hormones, vitamins and enzymes) wherein magnetically responsive, permeable, solid, water insoluble, microparticles are employed is disclosed in U.S. Pat. No. 4,115,534. U.S. Pat. No. 4,452,773 discloses magnetic iron-dextran microspheres which can be covalently bonded to antibodies, enzymes and other biological molecules and used to label and separate cells and other biological particles and molecules By means of a magnetic field. Coated magnetizeable microparticles, reversible suspensions thereof, and processes relating thereto are disclosed in U.S. Pat. No. 4,454,234. A method of separating cationic from anionic beads in mixed resin beds employing a ferromagnetic material intrinsically incorporated with each of the ionic beads is described in U.S. Pat. No. 4,523,996. A magnetic separation method utilizing a colloid of magnetic particles is discussed in U.S. Pat. No. 4,526,681. UK Patent Application GB 2,152,664A discloses magnetic assay reagents.

SUMMARY OF THE INVENTION

The method of the present invention is directed to the reversible aggregation of particles suspended in a liquid medium by employing a polyionic polymer to aggregate the particles and by contacting the aggregated particles with a chemical reagent capable of reversing the aggregation by cleaving the polyionic polymer. Where the particles in the medium are non-magnetic, they may form aggregates with each other, with other non-magnetic particles or with magnetic particles by addition of a polyionic polymer. Where the particles are magnetic, they may form aggregates with each other or with non-magnetic particles by addition of a polyionic polymer.

The method of the present invention has particular application in the assay of organic or biological analytes, particularly those analytes of interest in the analysis of body fluids. Of special interest are assays where the analyte is a member of a specific binding pair (sbp) where the analyte or an sbp member complementary to the analyte is bound, or can become bound, to the exterior surface of a particle. If the sbp member on the particle is not complementary to the analyte, then a complementary sbp member is also added. The method involves combining the particles which are suspended in liquid medium with an sbp member complementary to the analyte or to the sbp member on the surface and adding a polyionic polymer that is capable of non-specifically aggregating the particles. After aggregation has occurred, a chemical reagent that is capable of reversing the aggregation by cleaving at least some of the bonds of the polyionic polymer is added. Thereafter, the residual specific aggregation of the particles is measured. Normally, the sbp member is detected by virtue of a signal created by the use of a signal producing system that generates a signal in relation to the amount of the analyte in the sample.

Of special interest are methods such as removing cells from whole blood, where the analyte is a surface component or becomes bound to a non-magnetic particle. In such an instance, the method involves combining in the medium the sample including non-magnetic particles, such as whole blood, magnetic particles and a polyionic polymer for non-specifically agglutinating the magnetic particles and the non-magnetic particles, e.g. the cells. The medium is subjected to a magnetic field gradient to separate the agglutinated cells from blood plasma. The agglutinated cells are contacted with a chemical reagent under conditions for reversing the agglutination by at least partial depolymerization of the polyionic polymer.

The method of the invention provides a way of separating non-magnetic particles from a medium by virtue of non-specifically aggregating such particles to magnetic particles by employing a polyionic polymer. It also provides for reversing the aggregation by employing a chemical reagent that cleaves at least some of the bonds within the polyionic polymer.

The present invention also includes novel polyionic polymers including polycations of the formula:

$$(A)_n$$

wherein A is positively charged and has 4 to 30 atoms other than hydrogen, wherein the atoms are independently selected from the group consisting of carbon, oxygen, phosphorous, nitrogen and sulfur and wherein at least one of the A groups has a cleavable bond; and n is on the average 5 to 10,000.

Additionally, the invention includes kits for conducting the method of the invention and for conducting an assay for determining an analyte in a sample suspected of containing an analyte.

DESCRIPTION OF THE SPECIFIC EMBODIMENTS

The present invention relates to a method of reversible aggregation of particles suspended in a liquid medium. The method involves employing a polyionic polymer for aggregating particles or co-aggregating particles with each other and reversing the aggregation by employing a chemical reagent to cleave at least some of the cleavable bonds within the polyionic polymer. Oftentimes the particle to be separated from the liquid medium is a non-magnetic particle or will be aggregated to, or will be caused to aggregate to, a non-magnetic particle. On the other hand, sometimes the particle to be separated is magnetic or will be caused to co-aggregate with a magnetic particle. Therefore, by addition of a polyionic polymer in accordance with the present invention, aggregation will be achieved between non-magnetic particles, between magnetic and non-magnetic particles, or between magnetic particles.

In those cases where the particles to be separated from the liquid medium are magnetic or where magnetic particles are employed to co-aggregate non-magnetic particles, the aggregated particles are separated from the medium by the use of a magnetic field gradient. In those cases where magnetic particles are not employed, the aggregates may be separated from the liquid medium by use of any known method including but not limited to centrifugation, filtration, floatation, distribution between immiscible solvents, absorption onto selective sorbing media, and the like. The aggregated particles are treated with a chemical reagent capable of cleaving at least some of the bonds within the polyionic polymer for a time sufficient to reverse the aggregation.

Furthermore, the present invention relates to novel compositions for reversibly aggregating particles suspended in a liquid medium.

The compositions of the present invention are polyionic polymers of the formula:

$$(A)_n$$

wherein A is positively charged and has 4 to 30 atoms other than hydrogen, wherein the atoms are independently selected from the group consisting of carbon, oxygen, phosphorous, nitrogen and sulfur, and wherein at least one of said A groups has a cleavable bond; and n is an average of 5 to 10,000.

The preferred compositions are polyionic polymers of the formula:

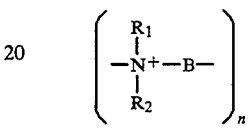

wherein $R_1$ and $R_2$ are the same or different and are independently selected from the group consisting of aryl, aralkyl, alkyl, alkylene and alkoxyalkyl groups of from 1 to 6 carbon atoms, and substituted aryl, aralkyl, alkyl, alkylene and alkoxyalkyl groups of from 1 to 6 carbon atoms. B is a linking group containing 2 to 30 atoms other than hydrogen which atoms are independently selected from the group consisting of carbon, oxygen, phosphorous, nitrogen and sulfur, wherein at least one of the B groups has a cleavable bond which when cleaved provides for a decrease in n, and n is an average of 5 to 10,000. The cleavable bonds are preferably in disulfides, carboxylic, phosphate, and sulfate esters and amides, carboboranes, siloxanes, vicinal glycols, and the like.

The reagents for cleaving the cleavable bonds include, but are not limited to, reducing agents such as mercaptans, such as dithioerythritol, hydrolyric enzymes such as pepsin, periodate salts, sulfite, phosphite and borohydride salts, hydrogen peroxide, and fluoride salts.

The present method has wide application in the field of the separation of suspended particles from a medium, particularly for separating biological materials such as cells and microorganisms, and in the fields of immunoassays and blood typing. The method provides for aggregating the particles using a polyionic polymer and for reversing the aggregation by addition of a chemical reagent capable of at least partially depolymerizing the polyionic polymer.

The invention provides a method for reversibly aggregating particles, which is more effective than, and eliminates the need for, reversing the ionic binding of particles by altering the ionic strength or the pH of the medium. The invention also has application to the assay of an analyte in a sample where a separation step is required.

Before proceeding further with the description of the specific embodiments of the present invention, a number of terms will be defined.

Analyte—the compound or composition to be measured, the material of interest. The analyte can De a member of a specific binding pair (sbp) and may be a ligand, which is mono- or polyvalent, usually antigenic or haptenic, and is a single compound or plurality of compounds which share at least one common epitopic or determinant site. The analyte can also be a component of a particle or can become bound to a particle during an assay. Exemplary of an analyte that is a component of a particle is an antigen on the surface of a cell such as a bloom group antigen (A, B, AB, O, D, etc.) or an HLA antigen. Exemplary of an analyte becoming bound to a particle during an assay is an sbp member where a complementary sbp member is bound to a particle, glycoprotein or glycolipids where a lectin is bound to a particle, antibodies where protein A is bound to a particle, and the like. The binding involved when an analyte becomes bound to a particle can be specific or non-specific, immunological or non-immunological.

The polyvalent ligand analytes will normally be poly(amino acids), i.e., polypeptides and proteins, polysaccharides, nucleic acids, and combinations thereof. Such combinations include components of bacteria, viruses, chromosomes, genes, mitochondria, nuclei, cell membranes and the like.

The precise nature of some of the analytes together with numerous examples thereof are disclosed in U.S. Pat. No. 4,299,916 to Litman, et al., particularly at columns 16 to 23, the disclosure of which is incorporated herein by reference.

For the most part, the polyepitopic ligand analytes employed in the subject invention will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

A wide variety of proteins may be considered as to the family of proteins having similar structural features, proteins having particular biological functions, proteins related to specific microorganisms, particularly disease causing microorganisms, etc.

The monoepitopic ligand analytes will generally be from about 100 to 2,000 molecular weight, more usually from 125 to 1,000 molecular weight. The analytes of interest include drugs, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which include cocaine and benzoyl ecgonine, their derivatives and metabolites, ergot alkaloids, which include the diethylamide of lysergic acid; steroid alkaloids; iminazoyl alkaloids; quinazoline alkaloids, isoquinoline alkaloids; quinoline alkaloids, which include quinine and quinidine; diterpene alkaloids, their derivatives and metabolites.

The next group of drugs includes steroids, which includes the estrogens, androgens, andreocortical steroids, bile acids, cardiotonic glycosides and aglycones, which includes digoxin and digoxigenin, saponins and sapogenins, their derivatives and metabolites. Also included are the steroid mimetic substances, such as diethylstilbestrol.

The next group of drugs is lactams having from 5 to 6 annular members, which include the barbiturates, e.g. phenobarbital and secobarbital, diphenylhydantonin, primidone, ethosuximide, and their metabolites.

The next group of drugs is aminoalkylbenzenes, with alkyl of from 2 to 3 carbon atoms, which includes the amphetamines, catecholamines, which includes ephedrine, L-dopa, epinephrine, narceine, papaverine, and their metabolites.

The next group of drugs is benzheterocyclics which include oxazepam, chlorpromazine, tegretol, imipramine, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs includes vitamins such as A, B, e.g. $B_{12}$, C, D, E and K, folic acid and thiamine.

The next group of drugs is prostaglandins, which differ by the degree and sites of hydroxylation and unsaturation.

The next group of drugs is antibiotics, which include penicillin, chloromycetin, actinomycetin, tetracycline, terramycin, the metabolites and derivatives.

The next group of drugs is the nucleosides and nucleotides, which include ATP, AND, FMN, adenosine, guanosine, thymidine, and cytidine with their appropriate sugar and phosphate substituents.

The next group of drugs is miscellaneous individual drugs which include methadone, meprobamate, serotonin, meperidine, amitriptyline, nortriptyline, lidocaine, procaineamide, acetylprocaineamide, propranolol, griseofulvin, valproic acid, butyrophenones, antihistamines, anticholinergic drugs, such as atropine, their metabolites and derivatives.

Metabolites related to diseased states include spermine, galactose, phenylpyruvic acid, and porphyrin Type 1.

The next group of drugs is aminoglycosides, such as gentamicin, kanamicin, tobramycin, and amikacin.

Among pesticides of interest are polyhalogenated biphenyls, phosphate esters, thiophosphates, carbamates, polyhalogenated sulfenamides, their metabolites and derivatives.

For receptor analytes, the molecular weights will generally range from 10,000 to $2 \times 10^8$, more usually from 10,000 to $10^6$ For immunoglobulins, IgA, IgG, IgE and IgM, the molecular weights will generally vary from about 160,000 to about $10^6$. Enzymes will normally range from about 10,000 to 1,000,000 in molecular weight. Natural receptors vary widely, generally being at least about 25,000 molecular weight and may be $10^6$ or higher molecular weight, including such materials as avidin, DNA, RNA, thyroxine binding globulin, thyroxine binding prealbumin, transcortin, etc.

Ligand analog or analyte analog—a modified ligand or ligand surrogate or modified analyte or analyte surrogate which can compete with the analogous ligand or analyte for a receptor, the modification providing means to join a ligand analog or analyte analog to another molecule. The ligand analog or analyte analog will usually differ from the ligand or analyte by more than replacement of a hydrogen with a bond which links the ligand analog or analyte analog to a hub or label, but need not. The term ligand surrogate or analyte surrogate refers to a compound having the capability of specifically binding a receptor complementary to the ligand or analyte. Thus, the ligand surrogate or analyte surrogate can bind to the receptor in a manner similar to the ligand or analyte. The surrogate could be, for example, an antibody directed against the idiotype of an antibody to the ligand or analyte.

Poly(ligand analog)—a plurality of ligand analogs joined together covalently, normally to a hub nucleus. The hub nucleus is a polyfunctional material, normally polymeric, usually having a plurality of functional groups, e.g., hydroxyl, amino, mercapto, ethylenic, etc. as sites for linking. The hub nucleus may be water soluble or insoluble, preferably water soluble, and will normally be at least about 30,000 molecular weight and may be 10 million or more molecular weight. Illustrative hub nuclei include polysaccharides, polypeptides (including proteins), nucleic acids, anion exchange resins, and the like. Water insoluble hub nuclei can also include walls of containers, e.g. glass or plastic, glass beads, addition and condensation polymers, Sephadex and Agarose beads and the like.

Member of a specific binding pair ("sbp member")—one of two different molecules, having an area on the surface or in a cavity which specifically binds to and is thereby defined as complementary with a particular spatial and polar organization of the other molecule. The members of the specific binding pair are referred to as ligand and receptor (antiligand). These will usually be members of an immunological pair such as antigen-antibody, although other specific binding pairs such as biotin-avidin, hormones-hormone receptors, nucleic acid duplexes, IgG-protein A, DNA-DNA, DNA-RNA, and the like are not immunological pairs but are included in the invention.

Ligand-any organic compound for which a receptor naturally exists or can be prepared.

Receptor ("antiligand")—any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, protein A, complement component C1q, and the like.

Non-magnetic Particles-diamagnetic or paramagnetic particles usually with a magnetic susceptibility ($\chi$) of less than $1 \times 10^{-5}$ emu/Oecm$^3$. The non-magnetic particles are generally at least about 0.02 microns and not more than about 100 microns, usually at least about 0.05 microns and less than about 20 microns, preferably from about 0.3 to 10 microns diameter. The non-magnetic particle may be organic or inorganic, swellable or non-swellable, porous or non-porous, preferably of a density approximating water, generally from about 0.7 to about 1.5 g/ml, and composed of material that can be transparent, partially transparent, or opaque. Usually the non-magnetic particles will have a charge, either positive or negative, and may have sbp members on their surface. Normally, the non-magnetic particles will be biologic materials such as cells and microorganisms, e.g., erythrocytes, leukocytes, lymphocytes, hybridomas, Streptococcus, *Staphylococcus aureus*, *E. coli*, viruses, and the like. The non-magnetic particles can also be particles comprised of organic and inorganic polymers, liposomes, latex particles, phospholipid vesicles, chylomicrons, lipoproteins, and the like.

The polymers will normally be either addition or condensation polymers. Non-magnetic particles derived therefrom will be readily dispersible in the assay medium and may be adsorptive or functionalizable so as to bind, either directly or indirectly, an sbp member or a magnetic particle.

Frequently, the non-magnetic particles will be an analyte, be bound to an analyte, or will become bound to an analyte during an assay. The non-magnetic particles not initially bound to the analyte can be derived from naturally occurring materials, naturally occurring materials which are synthetically modified and synthetic materials. Among organic polymers of particular interest are polysaccharides, particularly cross-linked polysaccharides, such a agarose, which is available as Sepharose, dextran, available as Sephadex and Sephacryl, cellulose, starch, and the like; addition polymers, such as polystyrene, polyvinyl alcohol, homopolymers and copolymers of derivatives of acrylate and methacrylate, particularly esters and amides having free hydroxyl functionalities, and the like.

The non-magnetic particles for use in assays will usually be polyfunctional and will have bound to or be capable of specific non-covalent binding to an sbp member, such as antibodies, avidin, bibtin, lectins, protein A, and the like. A wide variety of functional groups are available or can be incorporated. Functional groups include carboxylic acids, aldehydes, amino groups, cyano groups, ethylene groups, hydroxyl groups, mercapto groups and the like. The manner of linking a wide variety of compounds to particles is well known and is amply illustrated in the literature. See for example Cautrecasas, *J. Biol. Chem.*, 245 3059 (1970). The length of a linking group may vary widely, depending upon the nature of the compound being linked, the effect of the distance between the compound being linked and the particle on the binding of sbp members and the analyte and the like.

The non-magnetic particle will normally have an electronic charge, either positive or negative. The particle can be inherently charged or can be treated chemically or physically to introduce a charge. For example, groups such as carboxyl, sulfonate, phosphate, amino, and the like can be chemically bound to or formed on the particles by techniques known in the art. Cells are normally negatively charged due to the presence of sialic acid residues on the cell surface. Latex particles can be positively or negatively charged but normally will have a negative charge as a result of the introduction of functional groups or absorption of charged polymers such as polypeptides, proteins, polyacrylate, and the like.

The non-magnetic particles can be fluorescent or non-fluorescent, usually non-fluorescent, but when fluorescent can be either fluorescent directly or by virtue of fluorescent compounds or fluorescers bound to the particle in conventional ways. The fluorescers will usually be dissolved in or bound covalently or non-covalently to the non-magnetic particle and will frequently be substantially uniformly bound through the particle. Fluoresceinated latex particles are taught in U.S. Pat. No. 3,853,987 and are available commercially as Covaspheres from Covalent Technology Corp.

The fluorescers of interest will generally emit light at a wavelength above 350 nm, usually above 400 nm and preferably above 450 nm. Desirably, the fluorescers have a high quantum efficiency, a large Stokes shift and are chemically stable under the conditions of their conjugation and use. The term fluorescer is intended to include substances that emit light upon activation by electromagnetic radiation or chemical activation and includes fluorescent and phosphorescent substances, scintillators, and chemiluminescent substances.

Fluorescers of interest fall into a variety of categories having certain primary functionalities. These primary functionalities include 1-and 2-aminonaphthalene, p,p-diaminostilbenes, pyrenes, quaternary phenanthridine salts, 9-aminoacridines, P,P'-diaminostilbenes, imines, anthracenes, oxacarbocyanine, merocyanine, 3-aminoequilenin, perylene, bis-benzoxazole, bis-p-oxazolyl benzene, 1,2-benzophenazine, retinol, bis-3-aminopyridinium salts, hellebrigenin, tetracycline, sterophenol, benzimidazolylphenylamine, 2-oxo-3-chromen, indole, xanthene, 7-hydroxycoumarin, 4,5-benzimidazoles, phenoxazine, salicylate, strophantnidin, porpnyrins, triarylmethanes, flaying and rare earth chelates oxides and salts. Exemplary fluorescers are enumerated in U.S. Pat. No. 4,318,707, columns 7 and 8, the disclosure of which is incorporated herein by reference. Squaraine dyes described in U.S. patent application Ser. No. 773,401, filed Sep. 6, 1985 (the relevant disclosure of which is incorporated by reference) are also useful as fluorescers.

Additionally, light absorbent non-magnetic particles can be employed which are solid insoluble particles of at least about 10 nm in diameter.

Many different types of particles may be employed. Of particular interest are carbon particles, such as charcoal, lamp black, graphite, colloidal carbon and the like. Besides carbon particles metal sols may also fine use, particularly of the noble metals, gold, silver, and platinum.

Label—A member of the signal producing system that is conjugated to an sop member. The label can be isotopic or non-isotopic, usually non-isotopic, including catalysts such as an enzyme, a chromogert such as a fluorescer, dye or chemiluminescer, a radioactive substance, a particle, and so forth.

Signal Producing System—The signal producing system may have one or more components, at least one component being a label. The signal producing system generates a signal that relates to the presence or amount of analyte in a sample. The signal producing system includes all of the reagents required to produce a measurable signal. When the label is not conjugated to an sbp member analogous to the analyte, the label is normally bound to an sbp member complementary to an sbp member that is analogous to the analyte. Other components of the signal producing system can include substrates, enhancers, activators, chemiluminiscent compounds, cofactors, inhibitors, scavengers, metal ions, specific binding substances required for binding of signal generating substances, and the like. Other components of the signal producing system may be coenzymes, substances that react with enzymic products, other enzymes and catalysts, and the like. The signal producing system provides a signal detectable by external means, preferably by measurement of the degree of aggregation of particles or by use of electromagnetic radiation, desirably by visual examination. For the most part, the signal producing system will involve particles, such as fluorescent particles or other light absorbing particles, a chromophoric substrate and enzyme, where chromophoric substrates are enzymatically converted to dyes which absorb light in the ultraviolet or visible region, phosphors, fluorescers or chemiluminescers.

The signal producing system can include at least one catalyst, usually an enzyme, and at least one substrate and may include two or more catalysts and a plurality of substrates, and may include a combination of enzymes, where the substrate of one enzyme is the product of the other enzyme. The operation of the signal producing system is to produce a product which provides a detectable signal related to the amount of analyte in the sample.

A large number of enzymes and coenzymes useful in a signal producing system are indicated in U.S. Pat. No. 4,275,149, columns 19 to 29, and U.S. Pat. No. 4,318,980, columns 10 to 14, which disclosures are incorporated herein by reference. A number of enzyme combinations are set forth in U.S. Pat. No. 4,275,149, columns 23 to 28, which combinations can find use in the subject invention. This disclosure is incorporated herein by reference.

Of particular interest are enzymes which involve the production of hydrogen peroxide and the use of the hydrogen peroxide to oxidize a dye precursor to a dye. Particular combinations include saccharide oxidases, e.g., glucose and galactose oxidase, or heterocyclic oxidases, such as uricase and xanthine oxidase, coupled with an enzyme which employs the hydrogen peroxide to oxidize a dye precursor, that is, a peroxidase such as horse radish peroxidase, lactoperoxidase, or microperoxidase. Additional enzyme combinations may be found in the subject matter incorporated by reference. When a single enzyme is used as a label, other enzymes may find use such as hydrolases, transferases, and oxidoreductases, preferably hydrolases such as alkaline phosphatase and $\beta$-galactosidase. Alternatively, luciferases may be used such as firefly luciferase and bacterial luciferase.

Illustrative coenzymes which find use include AND[H]; NADP[H], pyridoxal phosphate; FAD[H]; FMN[H], etc., usually coenzymes involving cycling reactions, see particularly U.S. Pat. No. 4,318,980.

The product of the enzyme reaction will usually be a dye or fluorescer. A large number of illustrative fluorescers are indicated in U.S. Pat. No. 4,275,149, columns 30 and 31, which disclosure is incorporated herein by reference.

Magnetic particles—particles that are intrinsically magnetically responsive or have been rendered magnetic by, for example, attachment to a magnetically responsive substance or by incorporation of such substance into the particles. The magnetic particles can be paramagnetic, ferromagnetic, or superparamagnetic, usually paramagnetic and will have magnetic susceptibilities ($\chi$) of at least $5 \times 10^{-5}$ emu/Oecm$^3$, usually at least $4 \times 10^{-4}$ emu/Oecm3. The diameter of the particles should be small, generally in the range from about 5 nm to 50 microns, preferably from about 20 nm to 5 microns, more preferably from about 50 mn to 1 micron, frequently colloidal.

Exemplary of the magnetic component of particles that are intrinsically magnetic or magnetically responsive are complex salts and oxides, borides, and sulfides of iron, cobalt, nickel and rare earth elements having high magnetic susceptibility, e.g. hematite, ferrite. The magnetic component of other such particles includes pure metals or alloys comprising one or more of these elements.

For the most part the magnetic particles will contain a core of the magnetic component with surface functional groups such as hydroxyl, silicate, carboxylate, sulfate, amino, phosphate and the like. Frequently, an additional surface coating will be employed that is covalently or non-covalently bound to the surface. The surface coating can be an anionic or cationic detergent, usually anionic; or the coating can be a protein such as albumin, immunoglobulin, avidin, fetuin or the like; or it can be a carbohydrate such as dextran, chitosan, amylose and the like, or combinations or these substances in their native form or functionalized so as to control their charge and hydrophilicity. Alternatively, the particles can be coated with other amphiphilic substances such as lipopolysaccharides, octyl glucoside, etc.

Alternatively, the magnetic component can be incorporated into a particle such as, for example, impregnating the substance in a polymeric matrix. For a more in-depth discussion of the preparation of magnetic particles by this method, see Whitesides, et al. (1983) *Trends in Biotechnology*, 1(5):144–148 and references cited therein.

In those cases wherein it is desirable to use small magnetic particles, magnetic particles of less than a hundred nanometers in diameter can be made by precipitating iron oxides in the presence or absence of a coating such as a polysaccharide or protein. Magnetic particles of a few microns diameter can also be made by a ball milling process and removing material that is not in the size range of interest. Typically, magnetic particles formed by this latter process are quite polydisperse. Metal oxide suspensions that are generally monodisperse can be prepared by careful control of pH, temperature and concentrations during the precipitation process. Coating the magnetic particles with macromolecules can increase their colloidal stability. This can be done by direct adsorption of high molecular weight polymers or by functionalizing the surface of the particle and then binding macromolecules to the functional groups. Emulsion polymerization and grafting techniques provide a means for coating magnetic particles with polymers.

In general, the magnetic particle that is best for a given task will be determined primarily by the size and properties of the particles to be separated. For immunoassays or the isolation of cells, the magnetic particles preferably should be readily suspendable, form stable, preferably colloidal, suspensions, and have high magnetic susceptibility. Where an sbp member is bound to the surface, its ability to bind to a complementary sbp should be retained and should be stable with time.

Small (<100 nm) magnetic particles are advantageously used in immunoassays and cell separation procedures. These particles preferably have a homogenous core of metal, metal oxide or other metal compound. When colloidally stable, small particles can be suspended for long periods of time. Their large surface to volume ratio and relatively higher rates of diffusion enable them to quickly bind molecules and particles that are dispersed in the medium. Small magnetic particles are also less susceptible than large magnetic particles to aggregation due to residual magnetic moments after they have been exposed to a large applied magnetic field. Also, methods are known for colloidally stabilizing such small particles.

Magnetic particles of an intermediate size (100–1000 nm) can be suspended readily and require a lower surface charge density to prevent spontaneous aggregation than do smaller particles. Magnetic particles of this size range can be created by emulsion polymerization and have the advantage of a surface that is easily modified whether by grafting or the covalent bonding of macromolecules to their surface. However, they remain suspended for shorter times and their lower surface to volume ratio decreases the rate of binding to the substance to be separated.

Magnetic fluid—a colloidal suspension of magnetic particles in a liquid carrier that are not readily separated by a magnetic field. The resulting liquid has the bulk properties of a magnetic material. The fluid becomes spontaneously magnetized in the presence of an external magnetic field. The liquid also acts as a fluid and is capable of assuming the shape of its container, of flowing, and of moving around obstacles. Exemplary of a magnetic fluid is a ferrofluid where the suspended particles are ferromagnetic particles (see, for example, Rosenweig, supra, and U.S. Pat. No. 4,019,994, the disclosure of which is incorporated herein by reference, and Khalafolla, et al. (1980) *IEEE Transactions on Magnetics*, MAG-16:178–183).

The colloidal magnetic particles can be coated with protein material, e.g., a serum protein such as albumin, gammaglobulin, etc., and the like. The colloidal magnetic particles can be mixed with an aqueous buffered solution of protein to prepare the protein-coated colloidal magnetic particles. The coating of the magnetic particles with protein can be accomplished by physical (e.g., absorption) or chemical binding.

Non-specific binding—non-covalent binding between particles that is relatively independent of specific surface structures. Such non-specific binding will usually result from electrostatic interactions between oppositely charged particles or between particles having the same charge where a polyionic reagent having a charge opposite thereto is employed. Non-specific binding may also result from hydrophobic interactions between particles.

Polyionic polymer—a compound, composition, or material, either inorganic or organic, naturally occurring or synthetic, having at least five of the same charge, either polyanionic or polycationic, preferably at least ten of the same charge; e.g., a polyelectrolyte.

The polyionic polymer of the present invention is capable of aggregating particles in a liquid medium and has bonds capable of being cleaved by a chemical reagent to reverse the aggregation of the particles. Examples of cleavable bonds in the polyionic polymer are disulfides, carboxylic, phosphate and sulfate esters, amides, carboboranes, siloxanes, vicinal glycols, and the like.

Polyionic polymers useable in the present invention incude polymers having the following formula:

$$(A)_n$$

wherein A is positively charged and has 4 to 30 atoms other than hydrogen, where the atoms are independently selected from the group consisting of carbon, oxygen, phosphorous, nitrogen and sulfur, and at least one of the A groups has a cleavable bond; and n is an average of 5 to 10,000.

A preferred polycationic polymer of the present invention has the following structure:

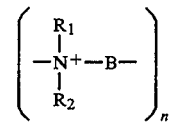

wherein
$R_1$ and $R_2$ are the same or different and are independently selected from the group consisting of aryl, aralkyl, alkyl, alkylene and alkoxyalkyl groups of from 1 to 6 carbon atoms, and substituted aryl, aralkyl, alkyl, alkylene and alkoxyalkyl groups of from 1 to 6 carbon atoms;

B is a linking group containing 2 to 30 atoms other than hydrogen which atoms are independently selected from the group consisting of carbon, oxygen, phosphorous, nitrogen and sulfur, and at least one of said B groups has a cleavable bond; and n is an average of 5 to 10,000. Preferably the cleavable bonds include disulfides or glycols.

Another preferred polycationic polymer has the aforementioned structure where $R_1$ and $R_2$ are the same or different and are independently selected from the group consisting of alkyl, alkylene and alkoxyalkyl groups of from 1 to 6 carbon atoms; B is independently selected from a group consisting of polyalkylene, or 0,0'bis-alkylenylpolyether, bis-alkylenyl disulfide and bis-alkylenyl ethylene glycol wherein at least one of the B groups has a disulfide or glycol group; and n is an average of 5 to 10,000.

Another preferred polycationic polymer has the aforementioned structure wherein $R_1$ and $R_2$ are the same or different and are independently selected from the group consisting of alkyl groups of from 1 to 4 carbon atoms; B is independently selected from a group consisting of $—(CH_2)_a—(S—S)_b—(CH_2)_c—$ where b is 0 or 1, a and c are from 2 to 8 when b is 1, and a and c are from 2 to 10 when b is 0, with the proviso that in at least one of the B groups b is 1; and n is an average of 10 to 10,000, and preferably n is an average of 10 to 20.

An additional preferred polycation has the aforementioned structure where $R_1$ and $R_2$ are methyl; B is $(CH_2)_m[CH(OH)]_2(CH_2)_p$, m and p are 1 to 8; and n is an average of 10 to 100. Another preferred polycation has the aforementioned structure wherein $R_1$ and $R_2$ are methyl; B is $—(CH_2)_a—SS—(CH_2)_c—$, where a and c are 3 to 5; and n is an average of 10 to 20.

Reversing agent—a chemical compound, composition, or material, either naturally occurring or synthetic, organic or inorganic, capable of reversing the aggregation of particles by at least partial depolymerization of the polyionic polymer. The reversing or cleaving agent acts upon the bonds of the polyionic polymer and cleaves on the average at least one bond per polymer, preferably at least 2 bonds per polymer.

The choice of specific reversing reagents depends on the cleavable bonds within the polyionic polymer. The following reversing agents are provided by way of example and are not meant to be a limitation on the scope of the present invention. Generally, the reversing agents are selected from the group consisting of hydrolyric enzymes, such as pepsin, trypsin, chymotrypsin, phosphobiesterase, and the like; mercaptans, for example mercaptoethanol, dithioerythritol, and glutathione, and the like; sulfite, halide, phosphate, periodate and borohydride salts; and peroxides, such as hydrogen peroxide.

As has been pointed out and by way of example, the specific reversing reagent chosen is dependent on the bonds that will be cleaved. For example, when the cleavable bond connects two sulfur atoms, the reagent selected will generally be a reducing agent such as, for example, dithioerythritol, and the like. Where the cleavable bond is a peptide bond, the reversing reagent may be trypsin, and the like. In cases where the cleavable bond connects the carbon atoms of a vicinal glycol, the reversing agent may be periodate, such as sodium periodate, and the like. Where the cleavable bond connects the carbon and oxygen atoms of an ester, the reversing agent may be chymotrypsin, sodium hydroxide and the like. Where the bond is a phosphate ester the reversing agent may be phosphodiesterase, and where the bond is carboborane the reversing agent may be hydrogen peroxide. Where the bond is siloxane the agent may be a fluoride salt.

Ancillary materials—various ancillary materials will frequently be employed in an assay in accordance with the present invention. For example, buffers will normally be present in the assay medium, as well as stabilizers for the assay medium and the assay components. Frequently, in addition to these additives, additional proteins may be included, such as albumins, or surfactants, particularly non-ionic surfactants, binding enhances, e.g., polyalkylene glycols, and the like.

As mentioned above, the present invention involves a method for reversibly aggregating particles dispersed or suspended in a liquid medium. The method comprises combining the liquid medium with a polyionic polymer. The polyionic polymers of the present invention are capable of aggregating the particles and are also capable of being cleaved so as to reverse the aggregation. The liquid medium containing the particles and the polyionic polymer is allowed to incubate for a time sufficient for aggregation of the particles to occur. Thereafter the aggregated particles are contacted with a chemical reagent that is capable of cleaving the polyionic polymer, under conditions, e.g., time, temperature concentration of reagent and the like to reverse the aggregation.

The particles to be separated will frequently be non-magnetic particles, or will be bound to non-magnetic particles, for example, red blood cells. In such cases, it is usually convenient to employ magnetic particles. Generally, coaggregation of the non-magnetic particles with magnetic particles is obtained by including magnetic particles and a polyionic polymer in the liquid medium. Where non-magnetic particles and magnetic particles are employed having the same charge, a polyionic polymer having an opposing charge is selected. After the medium is allowed to incubate for a time sufficient to form an aggregate, the medium is subjected to a magnetic field gradient to separate the aggregated particles from the medium. After the particles are separated from the medium the aggregation of the particles is reversed. In carrying out the method of the invention, the aggregation is reversed by contacting the particles with the reversing agent.

Moderate temperatures are normally employed for carrying out the method of the present invention and usually constant temperatures are used during the period for conducting the method. Generally, the temperatures will be chosen to promote aggregation or coaggregation of the particles by binding of the particles to the polyionic polymer. The temperature for the aggregation of the particles, particularly involving an assay, will generally range from about 0° to 50° C., more usually from about 15° to 40° C. Again, contacting the aggregated particles with the reversing agent, a temperature that promotes reversal of the aggregation or coaggregation of the particles by cleaving the polyionic polymer can be chosen. The temperature for the reversal of aggregation, particularly involving an assay, will generally range from about 0° to 50° C., more usually from about 15° to 40° C.

Where non-magnetic particles are to be separated from a medium, the concentration of the non-magnetic particles can vary widely depending upon the need. For example, in separation of cells from blood, the cell volume may represent fifty percent of the total volume of the blood. By contrast, it may be desired to separate as few as 1,000 bacteria/ml from a sample of water. When it is necessary to obtain non-magnetic particles that are relatively free of the medium as in an assay, usually the total volume of the non-magnetic particles should be less than five percent of the medium. In an assay where the analyte is a component of a particle or becomes bound to a particle, the analyte will generally vary from about $10^{-4}$ to $10^{-14}$M, more usually from about $10^{-6}$ to $10^{-12}$M.

In those instances where magnetic particles are added to the liquid medium in which particles of interest are suspended, the concentration of the magnetic particles added to the medium will depend on the quantity of particles in the medium that are to be separated, and the rate of separation that is desired, and the like. The concentration of magnetic particles will also depend on the magnetic field gradient and field strength, the magnetic susceptibility of the magnetic particles and the like. In general, the higher the concentration of magnetic particles added to aggregate the particles suspended in the liquid medium the more efficient and rapid will be the separation; however, too high a concentration can cause excessive entrainment of the medium. The concentration of magnetic particles added to the medium is normally determined empirically and will generally vary from about 0.1 to 1000 $\mu$g/ml, more usually from about 0.5 to 200 $\mu$g/ml, frequently from about 1 to 50 $\mu$g/ml.

In those instances where non-magnetic particles other than natural particles associated with the analyte are added to the medium in which particles of interest are suspended, their concentration will depend on numerous factors such as particle size and surface area, concentration of the particles in the medium, desired rate of separation and the like. In general, the concentration of non-magnetic particles added to the medium will normally be determined emperiodically and will generally vary from about 0.01 to 100 $\mu$g/ml, more usually from about 0.1 to 20 $\mu$g/ml. The concentration of non-magnetic particles will also depend on temperature, solubility, viscosity, the method of separation that will be employed and the like.

While the concentrations of the various reagents will generally be determined by the concentration range of interest of the particles to be aggregated and disaggregated with or without intervening separation procedures or the concentration range of the analyte in an assay, the final concentration of each of the reagents will normally Be determined empirically to optimize the rate and extent of aggregation, disaggregation and separation of the particles as the case may be and, in the case of an assay, the sensitivity and specificity of the assay over the range of interest. Other factors to be considered include non-specific and specific binding effects, desired rate of reaction, temperature, solubility, viscosity and the like.

The polyionic polymer for aggregating the particles is included in the liquid medium. As has been mentioned above, the polyionic polymer employed in the invention is capable of being at least partially depolymerized by a reversing reagent. The polyionic polymer has a charge opposite to that of the particles. The amount of polyionic polymer added should be sufficient so that substantially all of the particles become aggregated or coaggregated. This concentration may be determined empirically. Generally, the polyionic polymer will have a concentration in the liquid medium sufficient to provide a number of ions associated with the polymer and equal to the total number of charges of opposite sign on all the particles in the medium. In an assay, as discussed above wherein the analyte varies from about $10^{-4}$ to $10^{-14}$M, the polyionic polymer will have a concentration of about 10 nanomolar to 1 millimolar.

In an assay, the aqueous medium can also contain one or more members of a signal producing system. As mentioned above, the concentration of the various members of the signal producing system will vary and be dependent upon the concentration range of interest of the analyte and the type of measurement or assay involved. As a general point, the concentration of the various members of the signal producing system will be selected to optimize the signal produced in relation to the concentration range of interest of the analyte.

Non-specific aggregation will occur essentially instantaneously, and it is usually sufficient to allow the mixture to stand for 60 seconds, frequently less than 15 seconds. Where specific binding is required, the liquid medium is held for a period of time sufficient for binding to occur. Normally, this requires 0.5 to 120 minutes, more frequently 1 to 60 minutes.

In those instances where magnetic particles are employed, the magnetic field is applied preferably immediately after mixing. The extent of binding between the particles and the magnetic particles or between magnetic particles controls the efficiency of the magnetic separation. The application of a magnetic field to the medium to separate the particles from the medium can be carried out in a conventional manner that provides for a high magnetic field gradient. Normally, the method is conducted in a container made of non-magnetic material, for example, glass or plastic. In applying the magnetic field, the reaction container can be placed in close proximity to an electromagnet or permanent magnet, preferably permanent, which has a geometry to maximize the field intensity and gradient within the suspension. The higher the strength of the magnetic field and the higher the gradient, the faster the separation. Normally, it will be convenient to carry out the separation in a tube of diameter from about 2 to 50 mm, preferably from about 3 to 15 mm, with one or more permanent magnets mounted as close to the tube as practical to provide field strengths of at least about 200 Oe and preferably at least about 1 KOe with magnetic field gradients usually at least about 20 KOe/cm. The magnetic field is applied for a sufficient period of time to provide the desired degree of separation of the particles from the medium. Depending on the geometry, field strength, magnetic susceptibility of the particle and the like, the magnetic field is applied for a period of about 2 seconds to 1 hour, preferably about 5 seconds to 60 seconds.

Once the particles have been concentrated to one part of the container, the suspending liquid medium can be separated from the particles by any convenient means such as, for example, decantation, pipetting, and the like.

The present invention also has application in those instances where non-magnetic particles are to be separated from a liquid medium without employing magnetic particles. In such cases the aggregated non-magnetic particles may be separated from the medium by any convenient method. Such methods, include by way of example but not limitation, settling, centrifugation, floatation, distribution between immiscible solvents, filtration, absorption onto selective sorbing media, e.g., charcoal, silicates, resins, etc.; and the like.

The particles separated from the liquid medium are treated to reverse the aggregation of the particles. Generally, the particles are suspended in a liquid medium with a chemical reagent capable of reversing the aggregation.

The reversal of the aggregation of the particles and the coaggregation of the particles and the magnetic particles is effected by cleaving at least some of the bonds within the polyionic polymer. Therefore, the reversing agent chosen will be dependent on the polyionic polymer employed. Additionally, it is important to choose the reversing agent with regard to the nature of the particles in the aggregate so as to minimize or avoid damage to the particles after the reversal of the aggregation. The reversing agent selected will at least partially depolymerize the polyionic polymer employed to aggregate or coaggregate the particles.

The concentration of the reversing agent should be sufficient to result in substantial or complete reversal of the aggregation or coaggregation of the particles. The concentration of the reversing agent is generally dependent upon the nature of bonds of the polyionic polymer that are being cleaved. Generally, the concentration of the reversing agent will be at least equal to the concentration of the bonds to be cleaved, preferably at least ten times the concentration of the bonds, more preferably at least one hundred times the concentration of the bonds to be cleaved.

Depending on the strength and number of the bonds to be cleaved, and the nature and concentration of the reversing agent, the temperature and time needed for reversal of aggregation will vary. Generally, the temperature will range from about 0° to 45° C., more usually from about 15° to 40° C. Likewise, the time needed to reverse aggregation will range from about 0 to 45 minutes, usually from 15 to 40 minutes.

Once the particles have been separated from the aggregate, they may be used as desired. For example, in an assay the separated particles can be examined for the presence of a detectable signal in relation to the amount of an analyte in the sample. The separated particles can be cells which can be used as desired. For example, the separated particles can be red blood cells, test cells, and the like.

In a preferred embodiment of the invention, the magnetic particles are provided as a magnetic liquid, e.g., ferrofluid. The particles to be separated are combined with the magnetic liquid.

An important application of the present method is the removal of cells from a sample containing cells such as, for example, removal of red blood cells from whole blood. In the method, using whole blood by way of example and not by way of limitation, a whole blood sample is combined in a liquid medium with charged magnetic particles under conditions for non-specific binding of the magnetic particles to the cells in the presence of a polyionic polymer. The cells will usually have a negative charge by virtue of sialic acid residues or the like on the surface of the cells. Generally, the magnetic particles have a negative charge. A polycationic polymer capable of aggregating the particles and also having cleavable bonds such that reversal of said aggregation may be effected is included in the medium to provide conditions for non-specific binding between the cells and the magnetic particles. Polycationic reagents of the present invention described in detail herein are useful in this method.

Next, the medium can be subjected to a magnetic field gradient to separate the aggregated cells from the medium. Application of the magnetic field results in concentration of the cell-magnetic particle aggregate to one portion of the container, which permits its removal of the residual cell-free medium by, for example, decantation, piperring, etc.

The separated cell-magnetic particle aggregate can then be treated to release the cells from the aggregate as described above. The reversing reagent selected will be dependent on the nature of the bonds of the polycationic polymer as indicated above.

The present method provides particular advantages for automated blood typing procedures by providing a way to prepare blood plasma without centrifugation. It is also useful in the Coombs antiglobulin test where immunoglobulin-containing plasma is first combined with test cells and must then be fully removed in order to determine if antibodies from the plasma have bound to the cells. In this procedure magnetic particles and a polyionic polymer which acts as non-specific aggregating agent are added to the mixture of plasma and test cells and the subsequent separated cells are resuspended with the help of a reversing agent which cleaves the bonds of the polyionic polymer. Moreover, the present method can be employed in immunoassays wherein an spb member is bound to a particle and it is desired to separate and wash the particles without centrifugation; the particles can be magnetic or non-magnetic.

The present invention has application in general to assays for an analyte in a sample suspected of containing the analyte. The analyte is an spb member. In the assay the sample is combined in an assay medium with an spb member complementary to the analyte wherein at least one of the analyte or the complementary spb member is associated with the surface of a non-magnetic particle, usually a cell, such as an erythrocyte, a latex particle, or a magnetic particle. Charged magnetic particles are also combined with the medium under conditions for non-specific binding and aggregation of the particles by using a polyionic polymer to cause non-specific binding between the particles and magnetic particles. The present invention offers the improvement of reversing the aggregation using a chemical means to cleave the bonds of the aggregating polymer.

The assay will normally involve a signal producing system for producing a detectable signal in relation to the amount of analyte in the sample. The signal producing system usually includes a labeled sbp member. The medium may be further combined with none, one or more members of the signal producing system. Where magnetic particles are employed, the medium is subjected to a magnetic field gradient to separate aggregates comprising the magnetic particles from the medium. A chemical reagent capable of cleaving the polyionic polymer is added to the separated particles. The residual specific aggregation of the particles can then be measured. Such a determination can require the addition of any remaining members of the signal producing system not added above.

As a matter of convenience, the reagents for aggregating the particles and reversing the aggregation can be provided in a kit in package combination in predetermined amounts for aggregation and reversal of aggregation of a predetermined analyte. The kit can comprise a) a polymeric reagent for aggregating particles in a liquid medium and b) a reversing agent for reversing the aggregation of the particles by cleaving bonds within the polymeric reagent. Additionally, the kit can also include magnetic particles and/or ancillary agents as necessary.

As a matter of convenience, the reagents for conducting an assay can be provided in a kit in packaged combination in predetermined amounts for use in assaying for an analyte. The kit can comprise (a) an sbp member complementary to the analyte, (b) an sbp member bound to a charged particle if neither the analyte nor the complementary sbp member is bound to a charged particle, (c) charged magnetic particles if the charged particle is not magnetic, and (d) a polymeric reagent for non-specifically binding the magnetic particles or the magnetic particles and the non-magnetic particles wherein the polymeric reagent is capable of being cleaved by a chemical reagent whereby said nonspecific binding is reversed. Additionally, the kit can also include the chemical reagent for reversing the nonspecific binding and reagents for generating a signal in relation to the amount of analyte in the sample. Ancillary agents can be included as necessary for the particular assay.

EXAMPLES

The invention is described further by the following illustrative examples. All parts and percentages herein are by volume unless otherwise indicated. Temperatures are in degrees Centigrade (° C.). NMR spectra were run on a Varian T60 spectrometer. UV spectra were run on a Cary 210 spectrophotometer. Other spectrometers or spectrophotometers may be utilized.

Before describing the Examples a number of terms will be defined.

DEFINITIONS

Latex beads-0.297 μ acrylated polystyrene latex, surfactant free, from IDC of Portland, Oregon.

LISS-0.23M glycine, 0.029M NaCl, 0.0017M $KH_2PO_4$, and 0.0013M $Na_2HPO_4$, pH 6.7

KOH-potassium hydroxide $H_2O_2$-hydrogen peroxide

Polybrene-obtained from Sigma Chemical Company, St. Louis, MO.

DMSO-dimethylsulfoxide

DTE-dithioerythritol

Buffer-0.02M ammonium carbonate, pH 7.

EXAMPLE 1

Preparation of Disulfide of 2-Dimethylaminoethanethiol (1)

A homogeneous solution of 2-dimethylaminoethanethiol hydrochloride (14.2 g, 100 mmol) in methanol (50 ml) was stirred and cooled to 0° C. To the stirring chilled solution was added KOH (101 mmol) followed by slow addition of $H_2O_2$ (49.9 mmol). After 15 minutes, the methanol was evaporated, and the resultant mixture was extracted three times with ether. The ether extract was dried ($Na_2SO_4$), filtered, and evaporated to give 10.1 g of a pale yellow oil. Distillation of the oil under high vacuum gave 10 g of the disulfide (1) as a colorless liquid.

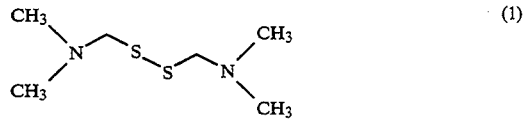

EXAMPLE 2

Preparation of ψ-Brene

Pseudobrene (ψ-Brene) was prepared using the two methods (A and B) below:

Method A: Diaminedisulfide (1) (1.043 g, 5 mmol) as prepared in Example 1 and 1,3-dibromopropane (1.03 g, 5 mmol) were added to about 4 ml of DMSO. The reaction was stoppered and stirred at room temperature. After 3-4 hours the reaction mixture was cloudy and after one day a white precipitate formed. After 7 days the reaction mixture was diluted with 5 ml of methanol and added to diethylether (100 ml) to form a white precipitate. The solid ψ-brene was collected by centrifugation. Purification of the solid by addition of methanol (5 ml) followed by precipitation by diethylether (100 ml) was repeated two more times. A portion of the solid was chromatographed on Sephadex G25 with 0.02M ammonium carbonate buffer.

Method B: Diaminedisulfide (1) (1.04 g, 5 mmol) and 1,3-dibromopropane (1.03 g, 5 mmol) were added to about 4 ml DMSO-$H_2O$ (75:25 v/v). The reaction mixture was stoppered and stirred at room temperature. The reaction mixture was cloudy and clarified in 3-4 hours. A total of 20 ml of water was added periodically over the next eleven days in proportions to bring the reaction to the cloud point. Thereafter, the water was evaporated. The product was precipitated using diethylether and a portion of the solid was chromatographed as in Method A.

NMR for Method A and Method B ($D_2O$) δ2.50 and 2.55 (small singlets, —N(C$\underline{H}_3$)$_2$ terminal groups), 3.3 (br s, $^+$NC$\underline{H}_3$) and 3.35-4.1 (m, C$\underline{H}_2$) ppm.

TABLE 1

| COPOLYMER | | A | B | C | D | E |
|---|---|---|---|---|---|---|
| 1,6-bisdimethyl-aminohexane | (mg) | 68.9 | 172.3 | 344.6 | 517.0 | 620.4 |
| | (mmol) | 0.4 | 1.0 | 2.0 | 3.0 | 3.6 |
| diaminedisulfide(l) | (mg) | 750.2 | 625.2 | 416.8 | 208.4 | 83.4 |
| | (mmol) | 3.6 | 3.0 | 2.0 | 1.0 | 0.4 |
| 1,3-dibromopropane | (mg) | 824.0 | 824.0 | 824.0 | 824.0 | 824.0 |
| | (mmol) | 4.0 | 4.0 | 4.0 | 4.0 | 4.0 |

EXAMPLE 3

Preparation of Copolymers

Copolymers of the diaminedisulfide (1) and 1,6-dimethylaminohexane with 1,3-dibromopropane were prepared in DMSO as specified in Table 1. The reactions and product isolations were carried out as in Example 1 except that ethylacetate was substituted for diethylether for the first two precipitations. Copolymers A and B were white powders; Copolymers C and D were gummy solids and Colpolymer E was a hygroscopic solid. Under high vacuum Copolymers C and D became glassy foams.

EXAMPLE 4

Preparation of Hydroxypolybrene

A mixture of 1,6-bisdimethylaminohexane (1.24 g, 5 mmol), DL-1,4-dibromo-2,3-butanediol (1,24 g, 5 mmol), and DMSO (3.5 ml) was stoppered and stirred. The initial two-phase mixture became homogeneous after 3 days. After 6 days the reaction mixture was added to 150 ml of anhydrous diethylether to give hydroxypolybrene as a gummy oil. A portion was further purified by dissolution in four times its weight in methanol, precipitation at $-78°$, and decantation of the cold supernatant.

NMR (methanol-d4): $\delta$0.3–2.3 (m, 8H, —NCH$_2$CH$_2$CH$_2$CH$_2$CH$_2$—); 2.9 (s, <1H, terminal N(CH$_3$)$_2$), 3.3 (br s, 12H, —$^+$N(CH$_3$)$_2$—) 3.4–3.8 (m, 8H, —$^+$N(CH$_3$)$_2$CH$_2$—), and 4.3–4.6 (m, 2H, CHOH) ppm.

Addition of acid shifted the terminal dimethylamine singlet downfield.

EXAMPLE 5

Preparation of Polymer from the Disulfide of 2-dimethylaminoethanethiol and 1,4-dibromobutane A solution of diaminedisulfide (1) (834 mg, 4.0 mmol) and 1,4-dibromobutane (864 mg, 4.0 mmol) in DMSO (2.8 ml) was stoppered and stirred. After 7 days the pasty mixture was diluted with methanol (5 ml), precipitated by dropping the resulting suspension into ethyl acetate (100 ml) and collected by centrifugation. The suspension, precipitation and centrifugation cycle was repeated two more times to give a white powder that was dried under vacuum.

EXAMPLE 6

Aggregation of Latex Particles by Polybrene and ψ-Brene

Test mixtures containing latex particles (0.88 mg/ml), ammonium carbonate buffer, and varying concentrations of an aggregating agent (Polybrene, ψ-brene, or hydroxypolybrene) were prepared and examined visually for aggregation after 0–60 seconds. Mixtures showing no aggregation were reexamined after 4–6 hours. Test mixtures containing clearly discernible aggregates were designated positive (+). Those remaining turbid with no discernible aggregates or settling after 6 hours were designated negative (−). Mixtures containing a few aggregates in a cloudy suspension and those containing cloudy suspension that settled in 6 hours were designated borderline (±).

Both high and low molecular weight column fractions of ψ-brene from Example 2 were tested. The disulfide of 2-dimethylaminoethanethiol (diaminedisulfide (1)) was used as a control. Results appear in Table 2 below.

TABLE 2

| Concentration in the test mixture | Polybrene | ψ-brene high mol. wt. | ψ-brene low mol. wt. | hydroxy-polybrene | di-amine control |
|---|---|---|---|---|---|
| 0 mg/ml | − | − | − | − | − |
| 0.025 mg/ml | − | − | − | − | − |
| 0.050 mg/ml | + | − | − | − | − |
| 0.100 mg/ml | + | ± | + | + | − |
| 0.200 mg/ml | − | + | + | + | − |
| 0.400 mg/ml | − | + | + | + | |
| 0.800 mg/ml | − | | | | |

The data in Table 2 show that all of the polymers tested caused aggregation of the latex particles. In each case the range of concentration of polymer that caused aggregation was at least a factor of two. Diaminedisulfide (1) control did not cause latex particle aggregation.

EXAMPLE 7

Prevention of ψ-Brene-dependent Aggregation

Test mixtures of latex particles (2.2 mg/ml) and DTE (1.22 mM) in ammonium carbonate buffer were treated with solutions of ψ-brene in ammonium carbonate buffer. The final mixture contained latex particles (0.88 mg/ml), DTE (0.49 mM) and ψ-brene (0.2 mg/ml). Both high-molecular-weight and low-molecular-weight column fractions of ψ-brene from Example 2 were tested. Polybrene (0.1 mg/ml in the final mixture) was used in place of ψ-brene as a control. Aggregation was detected visually as in Example 6.

The presence of DTE in the test mixtures prevented aggregation of latex particles by ψ-brene. This was observed for both high-molecular-weight and low-molecular-weight fractions of ψ-brene. Aggregation of latex particles by Polybrene was not prevented by addition of DTE.

EXAMPLE 8

Reversal of ψ-Brene-dependent, Aggregation

Aggregated test mixtures (500 ml) containing latex particles (0.88 mg/ml) and ψ-brene (0.2 mg/ml) in ammonium carbonate buffer were treated with aqueous DTE (10 μl of 25 mM). Both high-molecular-weight and low-molecular-weight fractions of ψ-brene from Example 2 were tested. Aggregated test mixtures containing Polybrene (0.1 mg/ml) instead of ψ-brene were used as controls. Aggregation was evaluated as in Example 6.

Dispersal of the latex particles aggregated with ψ-brene by DTE was seen. Substitution of H$_2$O for DTE did not produce aggregate dispersal. The procedure was repeated substituting Polybrene for ψ-brene. Neither DTE nor H$_2$O produced dispersal of latex particles aggregated by Polybrene.

EXAMPLE 9

Prevention of Hydroxypolybrene-dependent Aggregation

Test mixtures containing latex particles (2.2 mg/ml) and NaIO$_4$ (5 mM, 2.5 mM, 1.25 mM, 0.625 mM or OmM) in ammonium carbonate buffer were treated with hydroxypolybrene in ammonium carbonate buffer such that the final mixture contained latex particles (0.88 mg/ml), hydroxypolybrene (0.1 mg/ml) and NaIO$_4$ (2 mM, 1 mM, 0.5 mM, 0.25 mM, or 0 mM). Two sets of controls were done. In the first set NaIO$_4$ was replaced by an equivalent concentration of NaCl. In the second set hydroxypolybrene was replaced by Polybrene (0.1 mg/ml). Aggregation was evaluated visually as in Example 6.

A NaIO$_4$ concentration of 2 mM prevented immediate aggregation, whereas concentrations of 1 mM and 0.5 mM were initially borderline. After 16 hours mixtures containing greater than 0.5 mM NaIO$_4$ were no longer aggregated. Controls without NaIO$_4$ aggregated immediately and did not change, as did controls containing Polybrene.

EXAMPLE 10

Reversal of Hydroxypolybrene-dependent Aggregation

Aqueous NaIO$_4$ (10 µl, 5 µl, 1.5 µl, or 1.2 µl of O.1M) was added to test mixtures (500 µl) and hydroxypolybrene (0.1 mg/ml) in ammonium carbonate buffer. Two sets of controls were done. In the first set NaIO$_4$ was replaced by NaCl of equal concentration. In the second set hydroxypolybrene was replaced by Polybrene. Mixtures were examined visually for aggregation as in Example 6.

The aggregated latex particles containing hydroxypolybrene were dispersed immediately by the two higher NaIO$_4$ concentrations. After 16 hours all four NaIO$_4$ concentrations tested had caused dispersal of the aggregated latex particles, whereas without NaIO$_4$ the aggregates remained. Controls with NaCl and controls with Polybrene remained aggregated.

EXAMPLE 11

Aggregation of Blood by ψ-Brene and Copolymers

Blood (10 µl), LISS (85 µl), and a solution of the test polymer (15 µl) in LISS were mixed and evaluated visually for aggregation after 30 seconds as in Example 6. The polymers, their concentrations, and the aggregation performance appear in the Table 3 below. Copolymers were from Example 3 and ψ-brene was from Example 2.

TABLE 3

| Copolymer D | | Copolymer A | | ψ-Brene | |
|---|---|---|---|---|---|
| final concent. | Aggregation | final concent. | Aggregation | final concent. | Aggregation |
| 1.4 mg/ml | + | 1.4 mg/ml | + | 1.4 mg/ml | + |
| 0.68 mg/ml | + | 0.14 mg/ml | + | 0.68 mg/ml | + |
| 0.14 mg/ml | − | 1.4 µl.ml | − | 0.014 mg/ml | − |
| 0 mg/ml | − | 0 mg/ml | − | 0 mg/ml | − |

EXAMPLE 12

Prevention of Red Cell Aggregation

Test mixtures containing washed red blood cells (10 µl of 50% cells in LISS), aqueous DTE (5 µl of 25 mM) and LISS (95 µl) were prepared. Controls were prepared in which DTE was replaced by H$_2$O alone. An aqueous solution of ψ-brene (5 µl of 10 mg/ml) was added to each test mixture and control. Aggregation was evaluated visually as in Example 6 after 30 seconds.

The controls containing no DTE aggregated immediately, whereas aggregation was prevented in the test mixture containing DTE.

Red cell agglutination by Polybrene in a similar test is not affected by DTE.

EXAMPLE 13

Reversal of Red Cell Aggregation

Aggregated test mixtures of red cells were prepared by combining red blood cells (10 µl of 50% cells in LISS), LISS (95 µl) and an aqueous solution of ψ-brene (5 µl of 10 mg/ml). To the test mixtures was added aqueous DTE (5 µl of 25 mM). In a set of controls H$_2$O alone replaced the aqueous DTE. Aggregation was evaluated visually as in Example 6 after 30 seconds.

The test mixtures treated with DTE showed dispersal of the aggregated cells. The controls without DTE remained aggregated.

Red cells aggregated by Polybrene in a comparable experiment are not dispersed by DTE.

EXAMPLE 14

Preparation of Succinylated Magnetic Particles

Two hundred (200) mg of magnetic particles (Advanced Magnetic, BioMag 4100, 4 ml) were washed by magnetic separation (3×40 ml 0.1M phosphate buffer, pH 7.0) and resuspended in 15 ml of the above buffer. The particles were reacted with succinic anhydride (5 ml of 1M in DMF) by addition of 5 aliquots over 2 hours (the pH was adjusted to 7.0 following each addition). The succinylated particles were washed by magnetic separation (3×40 ml 0.1M phosphate buffer, pH 7.0, and 2×40 ml LISS), resuspended in 20 ml of LISS and stored at 4° C. with 0.02% sodium azide.

EXAMPLE 15

Whole Blood Separation

Whole blood (480 µl) was mixed with a solution of ψ-brene (80 µl of 20 mg/ml in LISS). A suspension of magnetic particles as prepared in Example 14 (2 mg in 248 ml of LISS) was added and the suspension mixed. The aggregates were separated magnetically. Separation was followed visually as the aggregated cells and magnetic particles were drawn toward the magnets. After 1 minute clear plasma was withdrawn by pipet.

Separation did not occur when ψ-brene was replaced by LISS alone.

EXAMPLE 16

Aggregation, Prevention and Reversal of Blood with Hydroxypolybrene

A. Aggregation

Blood (10 µl), LISS (95 µl), and a solution of hydroxypolybrene (5 µl of 100 mg/ml, 10 mg/ml, 1 mg/ml, or 0 mg/ml) in LISS were mixed and evaluated after 30 seconds for aggregation as in Example 6. Aggregation was observed with the two highest hydroxypolybrene concentrations tested.

B. Prevention

Blood (10 µl), LISS (95 µl), and aqueous NaIO$_4$ (5 µl of 25 mM) were combined in each test mixture. A solution of hydroxypolybrene (5 µl of 10 mg/ml) in LISS was added. Controls in which the NaIO$_4$ solution was replaced by H$_2$O were also done. Aggregation was evaluated visually after 30 seconds as in Example 6. No aggregation was seen when NaIO$_4$ was present. Aggregation was observed in the controls lacking NaIO$_4$.

Aggregation by Polybrene in a comparable experiment is not affected by NaIO$_4$.

C. Reversal

Aggregated test mixtures were prepared by combining blood (10 µl), LISS (95 µl) and a solution of hydroxypolybrene (5 µl of 10 mg/ml) in LISS. Aqueous NaIO$_4$ (5 µl of 25 mM) was added to each test mixture. Controls in which the NaIO$_4$ solution was replaced by H$_2$O alone were also done. Aggregation was evaluated visually after 30 seconds as in Example 6.

Aggregated cells were dispersed in the test mixtures containing NaIO$_4$. They were not dispersed in the controls that lacked NaIO$_4$.

In a comparable experiment, cells aggregated by Polybrene are not dispersed by NaIO$_4$.

The invention has been described in detail with particular reference to the above embodiments. It will be understood, however, that variations and modifications can be effected within the spirit and scope of the invention.

What is claimed is:

1. A method for assaying for the presence of an analyte that is a member of a specific binding pair (sbp), wherein said analyte or an sbp member complementary to said analyte is on the surface of particles suspended in a liquid medium comprising:
   combining said particles suspended in said liquid medium with an sbp member complementary to said analyte or to the sbp member on said surface;
   adding a polyionic polymer capable of non-specifically aggregating said particles;
   incubating said liquid medium for a time sufficient for non-specific aggregation of said particles to occur;
   adding to said liquid medium a chemical reagent capable of cleaving said polyionic polymer;
   incubating said liquid medium for a time sufficient to reverse said non-specific aggregation of said particles; and
   measuring the residual specific aggregation of said particles to determine the presence of said analyte,
   wherein said polyionic polymer is a polycation of the formula:

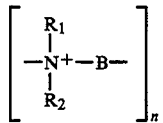

wherein
   $R_1$ and $R_2$ are the same or different and are independently selected from the group consisting of aryl, aralkyl, alkyl, alkylene, alkoxyalkyl, substituted aryl, substituted aralkyl, substituted alkyl, substituted alkylene, and substituted alkoxyalkyl with the proviso that the alkoxy of said alkoxyalkyls has from 1 to 6 carbon atoms and the alkyl in each of the above has from 1 to 6 carbon atoms;
   B is $-(CH_2)_a-(S-S)_b-(CH_2)_c-$, wherein b is 1, a and c are 2 to 8, and n is an average of 10 to 10,000.

2. The method according to claim 1 wherein said particles are biological particles.

3. The method according to claim 2 wherein said biological particles are selected from the group consisting of blood cells and microorganisms.

4. The method according to claim 3 wherein said blood cells are erythrocytes.

5. The method according to claim 1 wherein said particles are synthetic particles.

6. The method according to claim 1 wherein said particles are magnetic particles.

7. The method according to claim 1 wherein said particles are non-magnetic particles.

8. The method according to claim 7 wherein said non-magnetic particles are selected from the group consisting of liposomes and latex particles.

9. The method according to claim 1 wherein said polyionic polymer contains a cleavable bond and said reagent for cleaving said cleavable bond is selected from the group consisting of mercaptans, sulfite salts, borohydride salts, and peroxides.

10. In an assay for an analyte in a sample suspected of containing said analyte which analyte is a member of a specific binding pair (sbp) consisting of a ligand and its complementary receptor, said assay comprising the steps of combining the sample in an assay medium with an sbp member complementary to said analyte wherein at least one of said analyte and said complementary sbp member becomes bound to the surface of a non-magnetic particle, combining said medium with magnetic particles and a polyionic polymer for non-specifically binding said magnetic particles to said non-magnetic particles, subjecting said medium to a magnetic field gradient to separate said bound particles from said medium, and reversing the aggregation of said aggregated particles to determine the presence of said analyte, wherein the improvement comprises:
   employing as said polyionic polymer a reagent capable of being cleaved by a chemical reagent whereby said aggregation is reversed; and reversing said aggregation by addition of said chemical reagent,
   wherein said polyionic polymer contains a polycation of the formula:

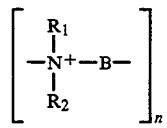

wherein
   $R_1$ and $R_2$ are the same or different and are independently selected from the group consisting of aryl, aralkyl, alkyl, alkylene, alkoxyalkyl, substituted aryl, substituted aralkyl, substituted alkyl, substituted alkylene, and substituted alkoxyalkyl with the proviso that the alkoxy of said alkoxyalkyls has from 1 to 6 carbon atoms and the alkyl in each of the above has from 1 to 6 carbon atoms;
   B is $-(CH_2)_a-(S-S)_b-(CH_2)_c-$, wherein b is 1, a and c are 2 to 8, and n is an average of 10 to 10,000.

11. A kit for conducting an assay for determining an analyte in a sample suspected of containing said analyte, said analyte being a member of a specific binding pair (sbp) consisting of a ligand and its complementary receptor, wherein said analyte is bound to a charged particle, said kit comprising (a) an sbp member complementary to said analyte, and (b) a polyionic polymer for non-specifically binding said charged particles, wherein said polyionic polymer is capable of being cleaved by a chemical reagent whereby said non-specific binding is reversed,
   wherein said polyionic polymer contains a polycation of the formula:

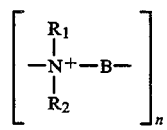

wherein
   $R_1$ and $R_2$ are the same or different and are independently selected from the group consisting of aryl, aralkyl, alkyl, alkylene, alkoxyalkyl, substituted aryl, substituted aralkyl, substituted alkyl, substituted alkylene, and substituted alkoxyalkyl with the proviso that the alkoxy of said alkoxyalkyls has from 1 to 6 carbon atoms and the alkyl in each of the above has from 1 to 6 carbon atoms;

B is $-(CH_2)_a-(S-S)_b-(CH_2)_c-$, wherein b is 1, a and c are 2 to 8, and n is an average of 10 to 10,000.

12. The kit according to claim 11 which further comprises said chemical reagent.

13. The kit according to claim 11 wherein said kit further comprises charged magnetic particles, wherein said polyionic polymer non-specifically binds said charged particles and said charged magnetic particles.

14. A kit for conducting an assay for determining an analyte in a sample suspected of containing said analyte, said analyte being a member of a specific binding pair (sbp) consisting of a ligand and its complementary receptor, said kit comprising (a) an sbp member complementary to said analyte bound to a charged particle, and (b) a polyionic polymer for non-specifically binding said charged particles, wherein said polyionic polymer is capable of being cleaved by a chemical reagent whereby said non-specific binding is reversed, wherein said polyionic polymer contains a polycation of the formula:

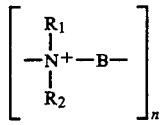

wherein

R$_1$ and R$_2$ are the same or different and are independently selected from the group consisting of aryl, aralkyl, alkyl, alkylene, alkoxyalkyl, substituted aryl, substituted aralkyl, substituted alkyl, substituted alkylene, and substituted alkoxyalkyl with the proviso that the alkoxy of said alkoxyalkyls has from 1 to 6 carbon atoms and the alkyl in each of the above has from 1 to 6 carbon atoms;

B is $-(CH_2)_a-(S-S)_b-(CH_2)_c-$, wherein b is 1, a and c are 2 to 8, and n is an average of 10 to 10,000.

15. The kit of claim 14 wherein said kit further comprises charged magnetic particles, wherein said polyioinic polymer non-specifically binds said charged particles and said charged magnetic particles.

16. A kit for conducting an assay for determining an analyte in a sample suspected of containing said analyte, said analyte being a member of a specific binding pair (sbp) consisting of a ligand and its complementary receptor, said kit comprising (a) a first sbp member complementary to said analyte, (b) a second sbp member bound to a charged particle, wherein said second sbp member is complementary to said analyte or to said first sbp member and (c) a polyionic polymer for non-specifically binding said charged particles, wherein said polyionic polymer is capable of being cleaved by a chemical reagent whereby said non-specific binding is reversed, wherein said polyionic polymer contains a polycation of the formula:

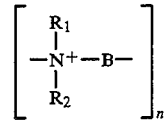

wherein

R$_1$ and R$_2$ are the same or different and are independently selected from the group consisting of aryl, aralkyl, alkyl, alkylene, alkoxyalkyl, substituted aryl, substituted aralkyl, substituted alkyl, substituted alkylene, and substituted alkoxyalkyl with the proviso that the alkoxy of said alkoxyalkyls has from 1 to 6 carbon atoms and the alkyl in each of the above has from 1 to 6 carbon atoms;

B is $-(CH_2)_a-(S-S)_b-(CH_2)_c-$, wherein b is 1, a and c are 2 to 8, and n is an average of 10 to 10,000.

17. The kit of claim 16 wherein said kit further comprises charged magnetic particles, wherein said polyioinic polymer non-specifically binds said charged particles and said charged magnetic particles.

* * * * *